United States Patent
Meijerink et al.

(10) Patent No.: US 10,881,614 B2
(45) Date of Patent: Jan. 5, 2021

(54) NICOTINAMIDE COMPOSITIONS AND THE THERAPEUTIC USE THEREOF

(71) Applicant: APeT Holding B.V., Ridderkerk (NL)

(72) Inventors: Hendrik Jan Cornelis Meijerink, Wespelaar (BE); Lekhram Changoer, IJsselstein (NL); Willem Blom, Berkel en Rodenrijs (NL); Marinella Regina Visser, Groningen (NL); Henderik Willem Frijlink, Groningen (NL); Anko Cornelus Eissens, Groningen (NL)

(73) Assignee: APeT Holding B.V., IJsselstein (NL)

( * ) Notice: Subject to any disclaimer, the term of this patent is extended or adjusted under 35 U.S.C. 154(b) by 0 days.

(21) Appl. No.: 15/718,000

(22) Filed: Sep. 28, 2017

(65) Prior Publication Data
US 2018/0140553 A1 May 24, 2018

Related U.S. Application Data

(63) Continuation of application No. 14/232,245, filed as application No. PCT/NL2012/050511 on Jul. 16, 2012, now abandoned.

(60) Provisional application No. 61/507,663, filed on Jul. 14, 2011.

(30) Foreign Application Priority Data

Jul. 14, 2011 (EP) .................................... 11173963

(51) Int. Cl.
| | | |
|---|---|---|
| A61K 9/48 | (2006.01) | |
| A61K 9/16 | (2006.01) | |
| A61K 9/00 | (2006.01) | |
| A61K 31/455 | (2006.01) | |
| A61K 9/20 | (2006.01) | |
| G01N 33/68 | (2006.01) | |
| A61K 31/198 | (2006.01) | |

(52) U.S. Cl.
CPC .......... *A61K 9/1652* (2013.01); *A61K 9/0065* (2013.01); *A61K 9/1635* (2013.01); *A61K 9/1641* (2013.01); *A61K 9/1676* (2013.01); *A61K 9/2054* (2013.01); *A61K 9/4808* (2013.01); *A61K 9/4891* (2013.01); *A61K 31/198* (2013.01); *A61K 31/455* (2013.01); *G01N 33/6893* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 3,976,794 A | 8/1976 | Watanabe et al. | |
| 4,973,467 A | 11/1990 | Sahley | |
| 4,980,168 A | 12/1990 | Sahley | |
| 5,057,323 A | 10/1991 | Niwa et al. | |
| 5,648,095 A | 7/1997 | Illum et al. | |
| 2007/0212411 A1 | 9/2007 | Fawzy et al. | |
| 2009/0104171 A1 | 4/2009 | Pardee et al. | |
| 2010/0285116 A1 | 11/2010 | Joshi | |
| 2011/0027376 A1 | 2/2011 | Boey et al. | |
| 2014/0234409 A1 | 8/2014 | Meijerink et al. | |

FOREIGN PATENT DOCUMENTS

| | | |
|---|---|---|
| EP | 2329810 A1 | 6/2011 |
| WO | 2010020098 A1 | 2/2010 |

OTHER PUBLICATIONS

English Translation of WO2010020098 retrieved from WIPO on Jul. 9, 2015.*
Tang, Y.; Venkatraman, S. S.; Boey, F. Y. C.; Wang, L. Sustained release of hydrophobic and hydrophilic drugs from a floating dosage form. Int. J. Pharm., 336, 2007, pp. 159-165 (Year: 2007).*
Welling, "Drug Toxicokinetics", Drug and Chemical Toxicology (1993) Marcel Dekker, Inc., (TOC only).
Arora, S. et al., "Floating drug delivery systems: A review", AAPS Pharmscitech. Springer New York LLC, US., vol. 6, No. 3, Oct. 19, 2005, pp. E372-E390.
Blom et al., "Neurologic Action of Megadoses of Vitamins", Bibithca Nutr Dieta (1986) No. 38, pp. 120-135.
Fanjiang, et al. "Nutrition and performance in children", Curr Opin Clin Nutr Metab Care, (May 2007) vol. 10, issue 3, pp. 342-347.
International Search Report of PCT/NL2013/050538.
Singh, B.N. et al., "Floating drug delivery systems: an approach to oral controlled drug delivery via gastric retention". Journal of Controlled Release, Elsevier, Amsterdam, NL, vol. 63, No. 3, Feb. 3, 2000, pp. 235-259.
Blom, W. et al. "Successful Nicotinamide treatment in an Autosomal Dominant Behavioral and Psychiatric Disorder", J, Inter. Metab. Dis., Suppl. 8, 1985, vol. 2, pp. 107-108.
Haslam, R. et al. "Effects of Megavitamin Therapy on Children with Attention Deficit Disorders", Pediatrics, Jul. 1984, vol. 74, No. 1. pp. 103-111.
Hoffer, A. "Vitamin B-3: Niacin and Its Amide", doctoryourself.com, 2011, 12 pgs.
International Search Report in PCT/NL2012/050511 dated Oct. 10, 2012.
Navab, F.et al. "Studies on intestinal absorption of amino acids and a dipeptide in a case of Hartnup disease", GUT, 1970, vol. 11, pp. 373-379.

(Continued)

*Primary Examiner* — Jessica Worsham
(74) *Attorney, Agent, or Firm* — N.V. Nederlandsch Octrooibureau; Catherine A. Shultz; Tamara C. Stegmann (57) ABSTRACT

The present invention relates to compositions and methods for the prophylaxis or treatment of deficiencies in essential amino acid absorption and metabolism and/or of a pathology or symptom associated therewith. In particular the invention concerns the treatment and/or prevention of ADHD, ADD and autism spectrum disorders. The present inventors have developed a method for prophylaxis or treatment of such symptoms and/or pathologies associated with a deficiency in essential amino acid absorption and/or metabolism, which method, stated generally, relies on the administration of nicotinamide, typically in a long-acting formulation so as to overcome the deficiencies of existing formulations, which have proven unsuitable for effective treatment.

10 Claims, 4 Drawing Sheets

(56) References Cited

OTHER PUBLICATIONS

Urine Indican Test (Obermeyer Test) Overview, Biohealth Diagnostics, Oct. 30, 2010, http://web.archive,org/web/20101030044926/http://biodia.com/general_content/indican_overview.html, 2 pgs.

Ghandforoush-Sattari et al., "Pharmacokinetics of Oral Taurine in Healthy Volunteers", SAGE-Hindawi Access to Research, Journal of Amino Acids, vol. 2010, Article ID 346237, 5 pages, doi:10.4061/2010/346237.

Stratford et al., "Nicotinamide pharmacokinetics in humans: effect of gastric acid inhibition, comparison of rectal vs oral administration and the use of saliva for drug monitoring", Britsh Journal of Cancer (1996) 74, 16-21.

Ellinger et al., "Tryptophan and the Biosynthesis of Nicotinamide", p. 276-281, Lister Institute of Preventive Medicine, London, S.W. 1, 1949.

Garten et al., "Nampt: Linking NAD biology, metabolism, and cancer", Trends Endocrinol Metab. Apr. 2009; 20(3): 130-138. doi:10.1016/j.tem.2008.10.004.

Hsu et al., "Nicotinamide phosphoribosyltransferase regulates cell survival through NAD+ synthesis in cardiac myocytes", Circ Res. Aug. 28, 2009; 105(5): 481-491. doi:10.1161/CIRCRESAHA.109.203703.

Blom, "Intestinal Tryptophan Uptake, Transport and Metabolism", W. Blom, Ansynth Service BV.

\* cited by examiner

NICOTINAMIDE COMPOSITIONS AND THE THERAPEUTIC USE THEREOF

FIELD OF THE INVENTION

The present invention relates to compositions and methods for the prophylaxis or treatment of deficiencies in essential amino acid absorption and metabolism and/or of a pathology or symptom associated there with. In particular the invention concerns the treatment and/or prevention of ADHD, ADD and autism spectrum disorders, which are typically associated with a deficiency in essential amino acid absorption and/or metabolism, especially tryptophan malabsorption.

BACKGROUND OF THE INVENTION

Attention deficit disorders, in particular Attention Deficit Hyperactivity Disorder (ADHD), are currently treated with methylphenidate. Ritalin is a short-acting formulation of methylphenidate. The long-acting formulation of methylphenidate is commercially available as Concerta. Methylphenidate is a psycho-stimulant drug and long-term side effects may include drug dependence, paranoia, schizophrenia, behavioural sensitization and psychotic symptoms such as hearing voices, visual hallucinations, urges to harm oneself, severe anxiety, euphoria, grandiosity, paranoid delusions, confusion, increased aggression and irritability. Other drugs used for the same purpose as methylphenidate are dexamphetamine (a psycho-stimulant drug), atomoxetine (Strattera; an anti-depressant) and niaprazine (a methylphenidate analogue), which generally suffer from similar draw-backs.

It has been suggested in the art that certain behavioral and/or psychiatric disorders like Attention Deficit Hyperactivity Disorder (ADHD) and Attention Deficit Order (ADD) may be associated with nutrient deficiencies.

Treatments of subjects suffering from ADHD and/or ADD involving nutritional supplements comprising nicotinic acid (niacin) has been suggested. Nutrient supplement compositions comprising Vitamin B3 are commercially available and sometimes manufacturers advertise that such preparations are useful to control ADHD and ADD. Such compositions are often in the form of capsules comprising e.g. about 5 mg vitamin B3. The recommended daily dose (RDA) of vitamin B3 is about 13 to about 18 mg for adults and about 9 to about 13 mg for children.

US 2009/0104171 discloses a nutritional supplement comprising acetyl-L-carnitine, α-lipoic acid, biotin, vitamin B1, L-glutamine, vitamin B6, taurine, folinic acid, vitamin B12, trimethylglycine and L-tryptophan for treating symptoms such as Attention Deficit Hyperactivity Disorder (ADHD). The nutritional supplement may further comprise vitamin B3. It may be in the form of an oral formulation, e.g. a tablet or a capsule.

Fanjiang and Kleinman, Curr. Opin. Clin. Nutr. Metab. Care 10, 342-347, 2007, disclose that multiple single micronutrient deficiencies have been associated with poorer cognitive performance, but that there is only little evidence that supports a causal role for such deficiencies in children with ADHD or autism spectrum disorders.

These and other teachings are however not based on any metabolic data that could provide the rationale for the diagnosis, proposed mechanism and suggested therapeutic treatment. As such the preparations comprise more or less arbitrary collections of nutritionally beneficial supplements employed at standard doses.

Haslam et al., Pediatrics 74(1), 103-111, 1984, disclose that megavitamin therapy (comprising administering nicotinamide) is ineffective in the treatment of ADHD.

Blom et al., J. Inher. Metab. Dis. 8, Suppl. 2, 107-108, 1985, and Blom et al., Biblthca Nutr. Dieta, 38, 120-135, 1986, disclose that nicotinamide (administered at a dosage of 20 mg/kg/day in six doses) had a beneficial effect on behavioral and psychiatric illnesses in three subjects that were suspected to suffer from tryptophan malabsorption. The research described in this document has not received much attention and there has never been any follow-up research in larger clinical setting. In any case, a significant disadvantage of the treatment described in Blom et al. lies in the need for frequent administration of oral nicotinamide. As will be recognized by those skilled in the art, treatment protocols requiring such frequent administration of medication are generally associated with poor patient compliance, even more so in the case of children.

The present inventors recognized the need for improvements in methods of prophylaxis and treatment of ADHD, ADD, autism spectrum disorders and other symptoms and/or pathologies associated with a deficiency in essential amino acid absorption and/or metabolism, especially with regard to side-effects and patient compliance. It is an objective of the present invention to provide such improvements. It is also an object of the invention to provide an improved oral nicotinamide formulation that allows for a highly effective and simple treatment regimen, with particular advantages with a view to dosing frequency and, hence, patient compliance. One further goal was to provide a delivery system that is simple and relatively cheap to manufacture.

SUMMARY OF THE INVENTION

The present inventors have developed a method for prophylaxis or treatment of ADHD, ADD, autism spectrum disorders as well as other symptoms and/or pathologies associated with a deficiency in essential amino acid absorption and/or metabolism, which method, stated generally, relies on the administration of nicotinamide, typically in a long-acting formulation.

On the basis of clinical experiments, the present inventors have established a correlation between deficiencies in the absorption and metabolism of certain (essential) amino acids, especially of tryptophan, and the occurrence of certain behavioral, psychiatric, neurological and somatic symptoms and pathologies.

The essential amino acid tryptophan is normally liberated in the small intestine by protein digestion. When tryptophan is absorbed over the intestinal wall serotonin is normally produced, which is necessary for the peristaltic movement of the intestinal system. The main part of absorbed tryptophan passes the liver via the vena portae, where 1 molecule $NAD^+$ is produced out of 60 molecules tryptophan. $NAD^+$ is e.g. important for energy metabolism and is then reduced to NADH. If NADH is recycled to $NAD^+$ by the respiratory chain massive amounts of ATP are produced. ATP is important for phosphorylation reactions and for the ion-pumps in the cells. $NAD^+$ is also phosphorylated to $NADP^+$ and NADPH, which is e.g. important for anti-oxidation reactions and the calcium homeostasis. In blood 85% of tryptophan is bound to albumin, which is important for tryptophan transport over the blood-brain barrier. The transported tryptophan will be converted in the serotonergic system to serotonin 5-OH-tryptamine-5-HT), necessary for cerebral neurotransmission.

Tryptophan malabsorption in the small intestine leads to less peristaltic movement due to a deficiency of serotonin in the intestinal wall. This will cause nutritional problems leading to e.g. deficiencies of vitamins and essential amino acids, etc., and to defecation problems (e.g. constipation). In young children this can also result in growth retardation.

Chronic tryptophan deficiency will lead to $NAD^+/NADH$ deficiency and secondary to less redox-reactions, and to ATP deficiency. Deficiency of $NAD^+/NADH$ leads further more to disorders of gene expression, cell death and aging. Secondary $NADP^+/NADPH$ deficiency will cause infections of the respiratory system, the skin and ears.

Tryptophan deficiency will cause diminished tryptophan transport over the blood-brain barrier, resulting in serotonin deficiency. The neurotransmission can also be diminished by problems in the ion-channels by insufficient working ion-pumps due ATP deficiency. Serotonin deficiency and impaired neurotransmission can lead to behavioral abnormalities (e.g. ADHD and ADD), neurological and/or psychiatric problems, epilepsy, and sleeping problems. Serotonin is also a precursor for the melatonin production in the Pine-apple gland. Melatonin regulates sleep an deficiency leads to sleep problems.

The present inventors have established that oral nicotinamide stimulates intestinal tryptophan absorption, resulting in a remarkable improvement of the intestinal peristaltic movement. Nutrition will normalize and deficiencies of (essential) amino acids and vitamins will disappear. Remarkable improvement up to normalization of behavioral, neurological and psychiatric abnormalities were observed, as will be described in greater detail in the appending examples.

Without wishing to be bound by any particular theory, it is hypothesized that after absorption, the nicotinamide can be converted to nicotinic acid, which can be metabolized in one or two steps in $NAD^+$, thereby relieving problems associated with $NAD^+/NADH$, the $NADPH^+/NADPH$ and the ATP deficiency and associated problems.

Nicotinamide is also believed to inhibit the first step of the kynurenine pathway resulting in less use of tryptophan to synthesize $NAD^+$, thus increasing (albumin bound) tryptophan available for transport over the blood-brain barrier. This will result in the stimulation of serotonin production and neurotransmission also due to the normalization of the ion-pumps and canals as the result of the increased of ATP production.

Normalization of serotonin production is also believed to normalize melatonin synthesis, and thus the treatment using nicotinamide may also aid in the relief of sleeping problems.

In a number of patients with epilepsy, behavioral and nutritional abnormalities antiepileptic, antidepressant and other drugs hardly improved the clinical picture. But under nicotinamide therapy the clinical picture normalized in one or two months.

Indican is one of the uremic toxins that accelerate the progression of chronic kidney disease (CDK), and may be also responsible for vascular disease via an induction of oxidative stress. Indican is a strong protein-bound uremic toxin, which has an important role in endothelial dysfunction, and deteriorate arteriosclerosis in renal failure patients. Because the intestinal tryptophan absorption is normalized by nicotinamide therapy, a normalization of indican in plasma and urine is observed, having a beneficial effect in chronic kidney disease patients and/or indican nephrotoxicity.

Hence, the present invention provides methods of treatment of the above symptoms and pathologies somehow associated to a deficiency in essential amino acid absorption and/or metabolism, using nicotinamide.

The absorption of nicotinamide occurs only in a limited (proximal) part of the GI-tract. Once this part of the GI-tract is passed by the nicotinamide dosage form, further drug release from the dosage form will result in limited or no absorption at all. Consequently, nicotinamide is absorbed only for a very limited period of time following oral administration. In addition, the present inventors believe that nicotinamide is cleared from the circulation rather rapidly. These effects seriously hamper the feasibility of nicotinamide treatments, because it would require the administration of a large number of nicotinamide unit doses throughout the day in order to maintain the nicotinamide level within the desired therapeutic window. The present inventors have realized that, for the development of satisfactory and practicable treatment, it is highly desirable to use a special delivery system which continuously releases nicotinamide during its residence the stomach while with gastric residence time is increased.

Thus, the present invention, in another aspect, provides a solution to these particular problems in the form of oral long acting nicotinamide formulation, which allows for absorption of nicotinamide into the systemic circulation from only a limited part of the (proximal) intestinal tract for an extended period of time after administration, by enhancing the gastrorentention or gastric residence time of the nicotinamide delivery system, during which nicotinamide is released from the system.

Surprisingly, the present inventors established that the use of oral long acting nicotinamide formulations allowed for effective treatment, not only with fewer dosages per day, but also with total daily dosages significantly below those suggested in the prior art. Hence, an aspect of the invention concerns treatment of deficiency in essential amino acid absorption and/or metabolism and associated symptoms and pathologies using specific dosage regimens.

Yet, another aspect of the invention concerns methods of diagnosing a deficiency in essential amino acid absorption and/or metabolism and associated symptoms and pathologies on the basis of urinary excretion of one or more indoles. Tryptophan not absorbed in the small intestine will enter the colon. The bacterial flora is then responsible for degradation reactions of tryptophan. One degradation product is indole. Passively absorbed indole is sulfonated in the liver and excreted in the urine as indican. By analysis of amino acids in a 24 hrs urine the amino acid excretion pattern can express (essential) amino acid (e.g. tryptophan and methionine) deficiencies, and vitamin (especially fat soluble vitamins, and vitamin B6 and B12) deficiencies. Hence, analysis of tryptophan, kynurenine pathway metabolites and indoles in a 24 hrs urine, gives information about intestinal malabsorption of tryptophan, increased production of bacterial tryptophan degradation products (especially indican), and insufficiency of the kynurenine pathway to synthesize $NAD^+$.

These and other aspects of the invention and its preferred embodiments will be described in more detail and exemplified in the following sections.

DETAILED DESCRIPTION OF THE INVENTION

A first aspect of the present invention concerns methods of treatment or prevention of a symptom or pathology associated with a deficiency in essential amino acid absorption and/or metabolism in a subject in need thereof wherein the method comprises the daily oral administration to said subject of S 5 separate dosage units containing nicotinamide in a total daily dosage of typically 10-500 mg/kg bodyweight; as well as the nicotinamide containing compositions for use in said methods of treatment.

In a particularly preferred embodiment of the invention, a method of treatment as defined above is provided wherein the symptom or pathology is a behavioral or psychiatric abnormality. Preferred behavioral or psychiatric abnormalities to be treated by the present methods include attention deficit hyperactivity disorder (ADHD); attention deficit disorder (ADD); autism spectrum disorders; apathy; anxiety; panic attacks; depression; obsessive-compulsive behaviour; hostility; hyperirritability; mania; memory loss; delirium; organic dementia; emotional lability; death wish; unmanageable behaviour, contact and play disability; restlessness; chaotic behaviour; stress-sensitive fits of crying and temper tantrums; and extreme sleeping difficulties. Most preferably the behavioral or psychiatric abnormality to be treated by the present method is Attention Deficit Hyperactivity Disorder (ADHD); Attention Deficit Disorder (ADD); or autism spectrum disorders.

In another particularly preferred embodiment of the invention, a method of treatment as defined above is provided wherein the symptom or pathology is a neurological disorder. Preferred neurological disorders to be treated by the present methods include neurological degeneration; epilepsy; psychomotor retardation; dizziness; bulbary paralysis; tremor, spasm; paresthesia; hyperesthesia; increased tendon reflexes; and disorientation. Most preferably the neurological disorder treated in accordance with the present invention is epilepsy.

In another particularly preferred embodiment of the invention, a method of treatment as defined above is provided wherein the symptom or pathology is somatic disorder. Preferred somatic disorders to be treated by the present methods include anorexia; glossitis; defecation problems, such as constipation; dermatitis; atopic eczema, sometimes accompanied by self-destructive scratching; and pellagra-like skin disorders. Most preferably the neurological disorder treated in accordance with the present invention is constipation.

In another particularly preferred embodiment of the invention, a method of treatment as defined above is provided wherein the symptom or pathology is chronic kidney disease and/or nephrotoxicity associated with tryptophan malabsorption, especially indican nephrotoxicity.

As explained herein before, the nicotinamide treatment, may also directly affect the deficiency in amino acid absorption and/or metabolism itself, apart from relieving the above listed symptoms and pathologies associated there with, e.g. by improvement of the intestinal peristaltic movement. Hence, also provided is a method of treatment or prevention of a deficiency in essential amino acid absorption and/or metabolism in a subject in need thereof wherein the method comprises the daily oral administration to said subject of ≤5 separate dosage units containing nicotinamide in a total daily dosage of 10-500 mg/kg bodyweight, as well as the nicotinamide containing compositions for use in said methods.

Essential amino acids cannot be synthesized de novo by humans, and therefore must be supplied in the diet. Of particular interest in the context of the present invention are those essential amino acids involved in neurotransmission and/or in the biosynthetic pathways of neurotransmitter substances, especially tryptophan, tyrosine, methionine and histidine. The present method is particularly effective in the treatment of symptoms and pathologies associated with deficiencies in tryptophan absorption and metabolism. Hence, in the most preferred embodiment of the invention, the essential amino acid is tryptophan.

As used herein, 'amino acid absorption' refers to the process of intestinal absorption of amino acids to enter the circulation. This is also sometimes referred to as amino acid resorption. For the purposes of the present invention, the terms are deemed synonymous and may be used interchangeably. In a particularly preferred embodiment of the invention, the deficiency in amino acid absorption is tryptophan malabsorption.

In the context of the present invention, 'amino acid metabolism' refers, in particular, to the processes of (i) biosynthesis of certain neurotransmitters, i.e. the biogenic amines (catecholamines and serotonin), from amino acids, especially the biosynthesis of serotonin from tryptophan; and (ii) the formation of $NAD^+/NADH$, $NADP^+/NADPH$ and ATP from tryptophan, in the kynurenine pathway. As explained herein before deficiencies in these metabolic processes may result in a variety of symptoms and pathologies and can be treated with nicotinamide. Hence in a preferred embodiment, the deficiency in amino acid metabolism is a deficiency in tryptophan metabolism, preferably a deficiency selected from kynurenine pathway deficiencies, especially $NAD^+/NADH$ deficiency, $NADP^+/NADPH$ deficiency, and/or ATP deficiency; and serotonin biosynthesis deficiencies.

The present method may involve both therapeutic (acute or chronic) and/or prophylactic (prevention) treatment of any one of the above recited disorders as appropriate.

Throughout this document, the person or animal to be treated will be described as the "subject", and it will be understood that the most preferred subject is a human and the invention will therefore be described with reference to the treatment of human subjects. However, it must be noted that the treatment of adverse conditions of the central nervous system in non-human animals are becoming more usual as well, such that the subject may also be an animal, especially an animal selected from the group of companion animals and livestock animals. The determination of an effective amount for a certain non-human animal is carried out in the same manner described below in the case of humans, and veterinarians are well accustomed to such determinations.

As will be understood on the basis of the foregoing, in accordance with the invention, the subject to be treated is typically a subject suffering from a deficiency in essential amino acid absorption or metabolism, preferably a subject suffering from tryptophan malabsorption or a deficiency in tryptophan metabolism, as described herein before. Most preferably the subject is a child suffering from tryptophan malabsorption.

In one particularly preferred embodiment of the invention the subject to be treated is a child, especially a child suffering from tryptophan malabsorption and/or showing behavioural abnormalities.

Nicotinamide (IUPAC name pyridine-3-carboxamide), also known as niacinamide and nicotinic acid amide, is the amide of nicotinic acid (vitamin B3/niacin). Nicotinamide is a water-soluble vitamin and is part of the vitamin B group. Nicotinic acid, also known as niacin, is converted to nicotinamide in vivo, and, though the two are identical in their vitamin functions, nicotinamide does not have the same pharmacologic and toxic effects of niacin, which occur incidental to niacin's conversion. Thus nicotinamide does not reduce cholesterol or cause flushing.

It will be understood by the skilled reader that nicotinamide, as well as other compounds used in the present invention, may be capable of forming salts, complexes, hydrates and solvates, and that the use of such forms in the defined treatments is contemplated herein. Nicotinamide preparations of high purities, e.g. of 97 or 99% purity, are commercially available. Such commercial preparations may suitably be used for preparing nicotinamide compositions for use in the present methods. Furthermore, synthesis methods of nicotinamide of high purity are known to those skilled in the art.

Nicotinamide lacks the vasodilator, gastrointestinal, hepatic, and hypolipidemic actions of nicotinic acid. As such, nicotinamide has not been shown to produce the flushing, itching, and burning sensations of the skin as is commonly seen when large doses of nicotinic acid are administered orally. The administration of substantial amounts nicotinic acid is not desired in accordance with the invention. In a preferred embodiment of the invention the composition used in the present method does not contain substantial amounts of nicotinic acid, e.g. it contains less than 5 wt %, preferably less than 1 wt %, more preferably less than 0.5 wt % of nicotinic relative to the amount of nicotinamide. Preferably the composition is entirely fee from nicotinic acid.

The effective amount of nicotinamide to be administered typically ranges from to 500 mg/kg daily. In one embodiment of the invention the treatment comprises the daily administration of >20 mg/kg, e.g. the daily administration of 21-500 mg/kg, more preferably of 25-250 mg/kg, most preferably of 30-100 mg/kg. Other treatment regimens which may be preferred in certain circumstances comprise the daily administration of <20 mg/kg, e.g. the daily administration of 10-19 mg/kg.

As will be understood by those skilled in the art, the treatments as defined herein above, may be applied for as long as desired or necessary with a view to the overall well-being of the subject to be treated. Typically the treatment comprises administering nicotinamide according to the present dosage regimens for a period of 2 weeks or more, preferably for a period of one month or more, more preferably for a period of more than 2, more than 3, more than 4, more than 6, more than 8, or more than 12 months. Given the fact that long-term use of nicotinamide is not expected to cause any serious adverse effects, there is no particular maximum to the period of treatment. Treatment will typically be ceased in case the nicotinamide is no longer required for proper absorption and/or metabolism of essential amino acids and/or for relieving symptoms or pathologies associated therewith.

As explained above, the merit of the invention, for one part, resides in the finding that a long acting formulation, especially a so-called gastroretentive delivery system, which will be described in much more detail below, allows for a highly effective and simple treatment regimen, with particular advantages with a view to dosing frequency and, hence, patient compliance. The present treatment thus preferably comprises the administration of not more than 5, preferably not more than 4, more preferably not more than 3 separate dosage units a day. Most preferably, the present method comprises administering nicotinamide dosage units to a subject once or twice a day only.

An important aspect of the present invention thus concerns the long-acting nicotinamide formulation per se as well as the use thereof for the treatment of any of the above described therapeutic purposes, especially a gastroretentive delivery system. As is known to those skilled in the art a gastroretentive delivery system is a device designed to be retained in the upper part of the gastrointestinal (GI) tract. Suitable examples include floating systems, raft systems, expanding systems, swelling systems, bioadhesive systems and low-density systems.

In a preferred embodiment the nicotinamide formulation of the invention is so-called floating drug delivery system (FDDS) that, upon administration to the subject to be treated, is capable of remaining in the stomach for a period extending over at least 2, at least 3, at least 4, at least 5 or at least 6 hours, typically in the fasted state. Furthermore, in a preferred embodiment of the invention the nicotinamide formulation is an FDDS that, upon administration to the subject to be treated, is capable of releasing nicotinamide to the GIT (stomach and proximal small intestine) for a period extending over at least 2, at least 3, at least 4, at least 5 or at least 6 hours, typically in the fasted state. Furthermore, in a preferred embodiment of the invention the nicotinamide formulation is an FDDS that, in a standard in vitro test in a so called USP dissolution apparatus, is capable of releasing nicotinamide from the delivery system in a so called slow release profile. Such a release profile is preferably characterized by a release of less than 45% of the total nicotinamide content after 1 hour and/or the release of more than 30% and less than 75% after 3 hours and/or the release of less than 80% after 6 hours. In an alternative embodiment the release profile is characterized by the release of less than 35% of the total nicotinamide content after 1 hour and/or the release of more than 30% and less than 75% after 5 hours and/or the release of more than 80% of the total nicotinamide content after 10 hours.

Unless specified otherwise in this document, in vitro testing of the gastro-retentive system is carried out in a so called USP dissolution apparatus II. With the dissolution medium (500 to 900 ml) at a temperature of 37° C. and a rotational speed of the paddle of 50 to 75 RPM. For investigating the release profile of the gastro-retentive systems, simulated gastric fluid of the following composition is used: sodium lauryl sulphate 2.5 g; sodium chloride 2.0 g; 0.01-0.05 N hydrochloric acid in water 1000 ml. Nicotinamide concentrations in the dissolution medium can be determined by any suitable analytical method, like ultraviolet absorption or HPLC analysis.

In a preferred embodiment of the invention the nicotinamide formulation is an FDDS, which remains buoyant on the gastric fluid upon administration, typically to achieve the afore-defined goals. Usually the buoyancy is characterized by the floating time (h) and/or buoyancy AUC (mg h). In a preferred embodiment of the invention a floating delivery system is provided and/or used having a floating time of at least 2, at least 3, at least 4, at least 5 or at least 6 hours when tested in vitro in the USP dissolution apparatus 11.

In a particularly preferred embodiment of the invention, and FDDS is provided comprising a particle having a hollow, gas-filled core bordered by a wall of at least one aqueous soluble, erodible, disintegrating or degradable polymer, said wall being surrounded by a coating comprising nicotinamide.

More preferably, in the FDDS of the invention nicotinamide is present in a coating that encompasses or surrounds a solid particle made of at least one aqueous soluble, erodible, disintegrating or degradable polymer (e.g. by coating onto the surface of the particle), said particle having a hollow, gas-filled core bordered by a wall of at least one degradable polymer. As will be understood, the gas is a non-toxic gas. Air is the preferred gas. Because of the gas-filled compartment, lacking any particulate matter or matrix components, a FDDS provided herein has unique floating capacity and therefore very good gastric retention properties. Using an established in vitro gastric fluid simulation system, a floating time of at least up to 24 hours was observed. Thus, provided herein is gastric retention device capable of remaining in the stomach for at least 6, preferably at least 9, more preferably at least 12 hours. Also provided is the use of an air-filled capsule, generally lacking any therapeutically active ingredient, as a floating carrier for a drug in a gastro-retentive drug formulation.

According to the invention, the active ingredient, typically nicotinamide is present in an outer layer or coating that controls not only the penetration of liquid (e.g. gastric fluid) into the particle, but also the release of nicotinamide from the particle. Thus, in contrast to floating systems known in the art comprising (sub)compartments or chambers filled with air, such as floating microspheres, the present invention is conceptually different in that the active ingredient is present on the exterior of the gas filled compartment, and essentially absent (at least upon manufacture) from the inner core of a particle.

As will be explained below, the particle may be a conventional gelatin or HPMC capsule known in the art, which is easily provided with a coating comprising nicotinamide. The system can be produced using only excipients that are known to be safe for human or animal use and that are accepted by regulatory authorities.

Typically, the particle in the FDDS of the invention itself will lack any therapeutically active ingredient and only contains nicotinamide in the external coating layer. However, it is also encompassed that a small (e.g. up to about 50%, preferably up to 35% or 30%, more preferably up to 20%, like 5, 10, 12, 15 or 17%) volume of the capsule or other type of hollow particle is filled with nicotinamide, or another active ingredient, as long as the overall density of the capsule remains sufficiently low to allow for floating. Therefore, also provided is the use of a capsule of which only 50% or less, preferred is 35% or less even more preferred 20% or less, of the volume is filled with nicotinamide or another active ingredient and the remaining volume is gas-filled as floating carrier for a drug in a gastro-retentive drug formulation. Only when the capsule erodes or disintegrates, its content is released. This may for instance be advantageous for applications wherein it is desirable to provide a final "burst" dose of the drug at the end of the release period. For example, a FDDS comprising the majority of nicotinamide in the particle coating and a minor fraction within the coated particle allows to achieve low yet sustained blood drug levels during the night, followed by an increased drug level in the morning. This is especially advantageous for the treatment of diseases wherein symptoms are worse in the morning, such as rheumatoid arthritis (RA) or asthma.

Since continued exposure of the stomach lining to nicotinamide may give rise to irritation, an embodiment is envisaged wherein the FDDS contains the nicotinamide in microencapsulate form, which microencapsulates are dispersed within the external coating layer of the FDDS. The microencapsulate typically contains a core comprising or consisting of nicotinamide covered by a layer of enteric polymer, designed to dissolve upon entry of the released microcapsules from the stomach into the small intestine. Alternatively the microencapsulate may simply comprise particles containing nicotinamide dispersed within an enteric polymer matrix, designed to dissolve upon entry of the released microencapsulate from the stomach into the small intestine.

The skilled person will be able to select the appropriate materials to obtain a coating, and optionally a micorencapsulate for incorporation in said coating, yielding the desired characteristics with respect to liquid penetration and the release of the nicotinamide in accordance with the afore described embodiments.

The nicotinamide may be present in two or more layers of the coating, each layer having a distinct composition. It is also possible to provide the particle with a "subcoating" and/or "topcoating" to achieve a desired GRT and/or release profile. A single coating layer comprising nicotinamide may be preferable in some embodiments for reasons of simplicity. However, in other preferred embodiments several layers of coatings may be applied, typically having distinct compositions and nicotinamide amounts. As will be shown in the examples, the use of two or three coating layers having distinct release profiles allows for the design of formulations capable of near constant nicotinamide release over periods of up to 12 hours. In one such embodiment an FDDS is provided comprising three coating layers, wherein the inner layer comprises 50-90 wt %, 60-87 wt % or 70-85 wt % of nicotinamide, based on the total weight of the inner coating layer; the middle layer comprises 30-70 wt %, 40-60 wt % or 45-55 wt % of nicotinamide, based on the total weight of the middle coating layer; and the outer layer comprises less than 10 wt %, less than 5 wt % or less than 1 wt % of nicotinamide based on the total weight of the outer coating. In another embodiment an FDDS is provided comprising two coating layers, wherein the inner layer comprises 50-90 wt %, 60-87 wt % or 70-85 wt % of nicotinamide, based on the total weight of the inner coating layer, and the outer layer comprises less than 10 wt %, less than 5 wt % or less than 1 wt % of nicotinamide based on the total weight of the outer coating layer.

The coating materials of the one or more coating layers may be selected from the group consisting of coating materials resistant to gastric juice, release-controlling polymers, and mixtures thereof. Release-controlling polymers are well known in the art of drug formulations for controlled (e.g. sustained) release, and include swellable polymers, or polymers that are poorly water-soluble or water-insoluble. Exemplary release controlling polymers are hydrophilic cellulose derivatives (such as HPMC, HPC, MC, HEC, CMC, sodium-CMC), PVP, PVA, Carboxyvinyl polymer (Carbomer), Poly(ethyleneoxide)(Polyox WSR), alginates, pectins, guar gum, vinylpyrrolidone-vinyl acetate copolymer, dextrans, carrageenan, gellan, hyaluronic acid, pullulan, scleroglucan, xanthan, xyloglucan, chitosan, poly(hydroxyethyl methacrylate), ammoniomethacrylate copolymers (such as Eudragit RL or Eudragit RS), Poly (ethylacrylate-methylmetacrylate) (Eudragit NE), and Ethylcellulose. The coating may comprise a mixture of at least two release controlling polymers. For instance, a combination of HPMC and Eudragit RL was found to be very useful. Eudragit RL PO is a polymer for controlled release drug formulation insoluble, pH independent with permeability and swelling properties. Due to the insolubility in the acid fluids of the stomach it is able to give a release of active ingredients over the desired period of time.

In another preferred embodiment, the invention provides a nicotinamide delivery system comprising a particle having a hollow, gas-filled core bordered by a wall comprising one or more coating layers comprising a combination of HPMC and starch as coating material, typically in a ratio within the range of 8:1-1:1, preferably 6:1-2:1, more preferably 5:1-3:1, most preferably about 4:1. The use of hypromellose was found to favourably delay nicotinamide release.

In preferred embodiments of the invention, an FDDS is provided comprising at least two nicotinamide containing coating layers, e.g. as described here above, having distinct ratios of hypromellose and starch, the outer layer typically comprising a larger amount of hypromellose, relative to starch, than the inner layer.

Furthermore, it has been established that coating layers comprising hypromellose or other water-swellable polymers maintained their favourable release profile and floating properties when mechanically damaged or even ruptured, as will be illustrated in the examples here below. Hence, a preferred embodiment of the invention concerns the FDDS as defined here above, and its use, wherein a polymer is used that swells upon contact with water, so as to render the FDDS 'self-repairing'. Most preferably said water-swellable polymer is hypromellose.

The FDDS coating may also comprise one or more enteric polymer coating materials. The term "enteric polymer" is a term of the art referring to a polymer which is preferentially soluble in the less acid environment of the intestine relative to the more acid environment of the stomach. Useful enteric polymers for practising the present invention include cellulose acetate phthalate, cellulose acetate succinate, methylcellulose phthalate, ethylhydroxycellulose phthalate, polyvinylacetatephthalate, polyvinylbutyrate acetate, vinyl acetate-maleic anhydride copolymer, styrene-maleic monoester copolymer, methacrylic acid methylmethacrylate copolymer, methyl acrylate-methacrylic acid copolymer, methacrylate-methacrylic acid-octyl acrylate copolymer, and combinations thereof.

In a specific aspect, the invention provides a nicotinamide delivery system comprising a particle having a hollow, gas-filled core bordered by a wall of at least one aqueous soluble, erodible, disintegrating or degradable polymer, said wall being surrounded by a coating comprising at least one enteric polymer and nicotinamide, preferably wherein the enteric polymer is a pharmaceutically acceptable methacrylic acid methylmethacrylate copolymer, such as a polymer sold under the trade name Eudragit™, including polymers from the Eudragit RL or Eudragit RS series. Again, mixtures of different types of coating polymers may be used. In one embodiment, the coating comprises a mixture of an enteric polymer, such as Eudragit RL, and a release controlling polymer. As is exemplified below, a combination of HPMC and Eudragit RL, for instance in relative weight ratio's of between 1:2 and 2:1, give very good results.

In addition to the coating polymer(s), a coating may comprise one or more additives having a beneficial or otherwise desired effect on a property of the coating. Useful additives include a plasticizer, a stabiliser, a pH adjuster, a GI motility adjuster, a viscosity adjuster, a diagnostic agent, an imaging agent, an expansion agent, a surfactant, and mixtures thereof.

In one embodiment, the coating comprises a plasticizer. The group of plasticizers contains, but is not limited to, materials such as PEG6000 (also known as Macrogol 6000), triethyl citrate, diethyl citrate, diethyl phthalate, dibutyl phthalate, tributyl citrate, and triacetin. The quantity of plasticiser included will be apparent to those skilled in the art. Typically the coating may include around 2-15 wt. % plasticiser based on the total dry weight of the coating. The enteric coating may also include an anti-tack agent such as talc, silica or glyceryl monostearate.

As will be understood, floating dosage forms rely on their ability to float on gastric fluid. Gastric fluid has a density close to that of water, which is 1.004 g/ml. Therefore, for the system to remain afloat, the overall density of the system must be less than 1 g/ml. In one embodiment, a drug delivery system according to the invention has a density of less than 0.95 $g/cm^3$. Lower densities, such as less than 0.9 $g/cm^3$, more preferably less than 0.8 $g/cm^3$ are of course preferred. In a specific aspect, the density is less than 0.7 $g/cm^3$.

Of particular interest is the inclusion in the coating comprising nicotinamide of an effervescent (gas forming) compound, i.e. an agent capable of generating $CO_2$ in situ upon contact with acid such as gastric fluid. This will provide the FDSS of the invention with additional buoyancy. Effervescent compounds are used already in the art of floating dosage forms and include sodium bicarbonate, sodium carbonate, or sodium glycine carbonate. However, the use of effervescent compounds has been limited primarily to either (a) single layer systems wherein gas forming material is mixed with the drug or (b) multiparticulate unit systems comprising a conventional sustained release pill, coated with a bilayer system consisting of an inner effervescent layer and an outer layer of swellable membrane (see Bardonnet et al. J Control Release 2006; 111(1-2)1-18).

The wall of the gas-filled particle is made of an aqueous soluble, erodible, disintegrating and/or biodegradable polymer such that the floating drug delivery system leaves no trace behind in the body. Suitable polymers that are aqueous soluble, erodible, disintegrating and/or biodegradable are well known in the art, and include gelatine and hydroxypropyl methylcellulose (HPMC).

The shape and size of the particle can vary. Of course, for oral administration purposes it is preferred that the particle can be swallowed. A preferred particle is a conventional gastric erodible/soluble capsule, such as a gelatine capsule or a HPMC capsule. Soft shells are also encompassed. The particle can be a single or a multiparticulate capsule. In one embodiment, the invention provides a FDDS comprising a capsule having a hollow, gas-filled core bordered by a wall of at least one aqueous soluble, erodible, disintegrating or degradable polymer, said wall being surrounded by a coating comprising at least one active ingredient. In view of gastric retention time, it is preferred that an oral gastro-retentive dosage form is as large as possible (to minimize passage through the pylorus) yet sufficiently small to be swallowed. Preferably, a FDDS provided herein comprises an oblong shaped capsule having a length of at least 10 mm, preferably at least 14 mm, more preferably at least 16 mm, most preferably at least 19 mm, and/or a diameter of at least 5 mm preferably at least 6 mm, more preferred at least 7, most preferred at least 8 mm. Suitable capsules include those referred to in the art as Type 5, 4, 3, 2, 2el, 1, 1el, 0, 0el, 00, 00el or 000 capsules. Alternatively, wide body capsules (BDCaps®) may be used. These capsules are referred to in the art as E, D, C, B, A, AA, AAel or AAA.

The FDDS as described herein provides an alternative gastro-retentive dosage form that is simple and relatively cheap to manufacture. A floating drug delivery system (FDDS) comprising nicotinamide can be prepared using a method comprising the steps of (a) providing a gas-filled particle made of at least one aqueous soluble, erodible, disintegrating or degradable polymer and (b) providing a coating dispersion comprising nicotinamide, a coating polymer, optionally additives, in a volatile solvent. Then, at least one layer of coating dispersion is applied onto the surface of particle, typically by spraying or dip coating. Application may be direct onto the aqueous soluble, erodible, disintegrating or degradable polymer making up the wall of the particle. Alternatively, the wall may first be provided with a sub-coating, on which the coating comprising active ingredient is applied. Upon the evaporation of the volatile solvent, a solid coating serving as "drug release layer" is obtained. Furthermore the nicotinamide-containing layer may be covered by a top-coating that improve the appearance of the capsule (e.g. giving it a colour) or contain taste-masking components. Step (a) preferably entails the manufacture of a conventional air-filled capsule according to well-established methods. The capsule can be a two-part conventional capsule as well as a single unit air filled capsule. Step (b) in itself is also standard practice in the art of controlled release dosage forms. The skilled person will be able to choose the type(s) and relative amount(s) of the components to obtain a coating dispersion that provides the particle with a drug coating having the desired release properties. A suitable volatile solvent is an alcohol, such as ethanol or isopropanol. Alternatively aqueous suspensions could be used. The dispersion may contain between about 10 and 600 gram of dry matter per liter solvent, such as between 50 and 150 gram per liter. The concentrations and relative amount of nicotinamide in the coating dispersion may depend on the dosage amount to be achieved. In general, the coating dispersion will contain between about 1 and 50 wt % nicotinamide based on the total dry weight of the dispersion. It is important that the coating dispersion is sufficiently homogeneous to obtain a good coating uniformity. This can be achieved by thorough mixing. When dip coating is applied even higher amounts of dry matter could be added to the volatile solvent. An aspect of the invention relates to the above-described methods for providing a floating drug delivery system (FDDS).

As will be illustrated in the examples here below, the FDDS of the present invention can be loaded with relatively high amounts of nicotinamide, i.e. as compared to other types of floating drug delivery systems. Depending on the target subject and/or dosage regimen, suitable dosage forms of the FDDS can be developed. In one embodiment, the FDDS comprises a particle (capsule) having a hollow, gas-filled core bordered by a wall of at least one aqueous soluble, erodible, disintegrating or degradable polymer, said wall being surrounded by a coating comprising 10 mg to 10 gram nicotinamide. Preferably, the coating comprises 20 to 8000 mg nicotinamide, more preferably 25 to 5000, such as 20-1000, 50-500 or 1000-2500. Preferred examples of the FDDS of the invention contain nicotinamide in a total amount of 100, 150 mg, 200 mg, 250 mg, 300 mg, 400 mg, 500 mg or 600 mg.

In an embodiment of the invention, the method comprises the co-administration of one or more additional ingredients selected from magnesium, taurine, tryptophan and zinc.

Supplementation of magnesium and taurine will aid in supporting the energy metabolism that will be stimulated by nicotinamide administration, as described herein above. The benefits of supplementation of taurine and/or magnesium will be most pronounced at the start of the nicotinamide treatment. Therefore, the present method may typically contain two distinct phases, wherein a first phase comprises taurine and/or magnesium supplementation and a subsequent phase comprises nicotinamide treatment without magnesium and/or taurine supplementation. Tryptophan supplementation may be particularly advantageous because nicotinamide treatment will result in enhanced absorption and metabolism of tryptophan in those patients in need thereof. Hence, in a preferred embodiment of the invention, the method comprised tryptophan supplementation.

As will be understood by those skilled in the art, it is particularly preferred to include the above additional ingredients, all of which are orally available and are normally administered orally, in the nicotinamide composition because this will avoid the need for (daily) intake of additional dosage units, which is desirable with a view to patient compliance. Hence, a preferred embodiment of the invention concerns a composition comprising nicotinamide, preferably an FDDS as defined herein above, further comprising one or more additional ingredients selected from magnesium, taurine, zinc and tryptophan; as well as the use of such compositions in the methods defined herein before.

Furthermore, an embodiment of the invention entails a kit of parts for use in the afore-defined methods, said kit of parts comprising one or more nicotinamide dosage units as defined herein before, preferably one or more of the afore-defined FDDS's containing nicotinamide, in combination with one or more further dosage units distinct from said first dosage unit in that it contains nicotinamide together with one or more additional ingredients selected from magnesium, taurine, tryptophan and zinc.

In another embodiment of the invention adjunctive therapy may be applied to treat the subject, typically a therapy conventionally applied in treatment of one of the present pathologies. The effects attained by the present method and the adjunctive therapy may be fully additive. The effect attained may even be synergistically enhanced. Furthermore, the aim of combining the present method with a therapy conventionally applied could be the lowering of the doses usually required to attain the optimal effect, e.g. to significantly reduce the side effects associated with the conventionally applied therapy. In such embodiments, the method may typically comprise the co-administration of an adjunctive active substance, in any manner which provides effective levels thereof in the body. The expression "active ingredient" refers to any compound having biological activity, or being capable of being converted to such compound (e.g. a pro-drug). If the adjunctive substance is orally available and is normally administered orally, oral administration thereof is preferred. It may be administered together with nicotinamide, in a single dosage form, or may be administered separately. It is particularly preferred, however, for the adjunctive combination to be administered as a single pharmaceutical composition, so pharmaceutical compositions incorporating both nicotinamide and an adjunctive active substance, such as a substance selected from stimulant medication like methylphenidate; dexamphetamine; atomoxetine; niaprazine; selective norepinephrine reuptake inhibitors (SNRIs) like atomoxetine; selective serotonin and norepinephrine reuptake inhibitors (SSNRIs); selective serotonin reuptake inhibitors (SSRIs), such as bupropion, guanfacine and clonidine; antidepressants including the monoamine oxidase inhibitors (MAOIs), tricyclic antidepressants (TCAs), tetracyclic antidepressants (TeCAs), selective serotonin reuptake inhibitors (SSRIs), serotonin-norepinephrine reuptake inhibitors (SNRIs); stimulants like caffeine, nicotine, amphetamines, MDMA, cocaine, NRIs & NDRIs, modafinil, adrafinil, armodafinil, ampakines, tryptamines like yohimbine; and antipsychotics including those that block D2 and other receptors in the dopamine pathways; as well as the use of such compositions, are important embodiments of the present invention. In such embodiments, each dosage unit may contain the daily doses of nicotinamide and the adjunctive substance, or may contain a fraction of the daily doses, such as one-third or half of the doses. Alternatively, each dosage unit may contain the entire dose of one of the compounds, and a fraction of the dose of the other compound. In such case, the subject would daily take one of the combination dosage units, and one or more units containing only the other compound. The amounts of each drug to be contained in each dosage unit depends on the identity of the drugs chosen for the therapy, and other factors such as the indication for which the adjunctive therapy is being given Hence, the invention also entails a kit of parts for use in the afore-defined methods, said kit of parts containing one or more nicotinamide dosage units as defined herein before, preferably one or more FDDS's, together with one or more dosage units distinct from said first dosage units in that they contain an active substance for adjunctive therapy as explained in the foregoing passages.

Another aspect of the invention concerns a method of diagnosing a deficiency in essential amino acid absorption and/or metabolism in a subject, said method comprising determining the urinary excretion of one or more indoles, preferably indican, typically in a 24 h urine.

In another embodiment of the invention a method of diagnosing a pathology or symptom selected from behavioral and psychiatric abnormalities, neurological disorders and symptomatic disorders, as defined herein before, said method comprising determining the urinary excretion of one or more indoles, preferably indican, typically in a 24 h urine. As will be understood on the basis of what has been described here above, the aim of such diagnosis is typically to associate the behavioural, psychiatric, neurological or somatic symptom presenting in the subject to a deficiency in essential amino acid absorption and/or metabolism, especially to a deficiency in tryptophan absorption. If the diagnosis confirms such deficiency the subject will be responsive to nicotinamide treatment in order to relief the behavioural, psychiatric, neurological or somatic symptom and/or to treat the underlying cause. The method of diagnosis may also suitably be employed to monitor development of the deficiency and/or the response to treatment.

Typically the method comprises the steps of collecting one or more urine samples of a subject, analysing the urine samples in order to quantify the amount of one or more indoles in said one or more samples and comparing said quantity with predetermined standard values representative of healthy and diseased state. It will be apparent to those skilled in the art how to perform such analyses using standard techniques such as TLC, HPLC and GC-MS.

In a preferred embodiment of the invention the method comprises the step of administering a predetermined amount of tryptophan, following which the urine samples are collected and analysed in order to quantify the amount of one or more of kynurenine, N-acetylkynurenine, 3-hydroxykynurenine, kynurenic acid and xanthurenic acid and comparing said quantity with predetermined standard values representative of healthy and diseased state.

As will be understood by those skilled in the art, the principal features of this invention can be employed in the various aspects and embodiments without departing from the scope of the invention. More, in particular, it is contemplated that any feature discussed in this specification can be implemented with respect to any of the methods, compositions and uses of the invention, and vice versa.

Furthermore, for a proper understanding of this invention and its various embodiments it should be understood that in this document and the appending claims, the verb "to comprise" is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The following examples describe various new and useful embodiments of the present invention. It will be understood that particular embodiments described herein are shown by way of illustration and not as limitations of the invention. Those skilled in the art will recognize, or be able to ascertain using no more than routine experimentation, numerous equivalents to the specific procedures described herein. Such equivalents are considered to be within the scope of this invention and are covered by the claims.

Example 1

A typical example of a gastro-retentive system can be obtained by coating of an empty gelatine capsule with coating comprising at least one pharmacologically active ingredient.

In a specific embodiment the gelatine capsule is coated with a suspension containing:

| | |
|---|---|
| drug (e.g. nicotinamide) | 1 to 95% of the solids in the suspension; |
| polymers and release controlling agents: | 5 to 99% of the solids in the suspension. |

The amount of drug that will be sprayed onto the capsule is determined by the desired dose of the drug and the concentration of the drug in the coating. The composition of the drug containing coating layer is determined by the desired release profile. Typical polymers like Hypromellosum 4000 mPa·s, viscosity2% m/V or Eudragit RL PO can be used whereas plasticizers such as Polyethylenglycolum 6000 or dibutyl phthalate can be used. Other excipients that can be used in the coating suspension are magnesium stearate, talc or mannitol. The coating suspension is applied on the gelatine capsules in equipment such as fluidized beds or perforated pan-coaters.

A second example of a gastro-retentive system can be obtained by the incorporation of gas-forming materials in a tablet that contains a hydrophilic gel forming polymer.

In a specific embodiment such a tablet would contain:

| | |
|---|---|
| drug | 0.5 to 90%; |
| HPMC 4000 | 10 to 80%; |
| sodium carbonate | 5 to 20%; |
| Sodium stearyl fumarate | 0.5 to 5%. |

Furthermore excipients such as fillers, binders, glidants, lubricants and others known in the art of tablet formulation can be added to the formulation. The tablets can be made according to well known tablet production technologies such as direct compaction, dry granulation or wet granulation techniques. Tablet compaction can be performed using tablet machines widely known in the pharmaceutical industry.

Example 2: Dissolution of Nicotinamide from FDDS

Materials

HPMC (Hypromellosum 4000 mPa·s, viscosity 2% mN) was obtained from Bufa BV, Uitgeest, The Netherlands. Macrogol 6000 (Polyethylenglycolum 6000) was obtained from Fagron, The Netherlands. Eudragit RL PO (Pharma Polymere, Röhm GmbH) was obtained from Chemische Fabric, Kirschenallee, Darmstadt, Germany. Nicotinamide Ph.Eur.quality was used.

Methods

A number of different coating dispersions (also referred herein as "suspensions") were prepared (see Table 1). The required amount of HPMC was weighted to a beaker and then mixed with Ethanol (100 ml). Subsequently, the nicotinamide was added in the amounts indicated below. In parallel, in another beaker Macrogol 6000 was prepared by melting at a temperature not higher than 80° C., after melting, ethanol (50 ml) was added and subsequently the required amount of Eudragit RL PO was added. The cooled solution was mixed with the contents of the first beaker to provide a coating dispersion.

TABLE 1 composition of the different coating suspensions.

| Ingredient | Coating 1 | Coating 2 | Coating 3 |
| --- | --- | --- | --- |
| HPMC | 4.0 g | 4.0 g | 5.0 g |
| Eudragit RL PO | 3.5 g | 3.5 g | 3.5 g |
| Macrogol 6000 | 1.0 g | 1.0 g | 1.0 g |
| nicotinamide | 5.0 | 1.0 | 5.0 |
| ethanol | 150 ml | 150 ml | 150 ml |

Hard gelatine capsules (No. 3) were coated with the different coating dispersions using an appropriate spray nozzle according to standard procedures. Briefly, the coating dispersion was sprayed onto the surface of the capsules rotating in a small container under a heated air stream until the required amount of drug-polymer mixture as determined by weight analysis was sprayed on the capsules.

Dissolution test were performed in a beaker with 500 ml of 0.1 M HCl at pH=1.03-1.09 at a temperature of 34-38° C. while stirring at 150 rpm using a magnetic stirrer.

Samples (2.5 ml) were taken every 30 minutes up to 7 hours with a syringe. The samples were analysed at 280 nm for the content of active ingredients using a spectrophotometer.

Results

Four capsules were coated with coating dispersion 1, and two of them were subjected to the dissolution test in a beaker with 500 ml of 0.1N HCl. After six hours, more than 95% of active substance was released, showing that drug release was complete after 6 hours. The capsule was still floating on the 0.1N HCl after 24 hours.

Coating dispersion 2 was used to coat four capsules, and two of them were subjected to the dissolution test. After six hours, more than 90% of active substance was released. The capsule was still floating on the 0.1N HCl after 24 hours.

Coating dispersion 3 was used to coat another four capsules and two of them were subjected to the dissolution test. After six hours, less than 50% of active substance was released. The higher quantity of HPMC in coating 3 leads to a slower release of active substance. Moreover the release was incomplete. This shows that, by varying the polymer content of the coating composition, the rate of drug release from the floating particle can be altered. The capsule was still floating on the 0.1N HCl after 24 hours.

Example 3: Development of a 300 mg and a 600 mg Nicotinamide Gradient FDDS

BACKGROUND

The concept of an FDDS comprising several layers of distinct composition and distinct amounts of nicotinamide was tested. Also the concept of an FDDs comprising an outer coating layer comprising no nicotinamide was tested.

The aim of the experiment was to optimize the formulation, especially to prevent an initial release burst and to prolong the period of constant nicotinamide release, preferably over the entire residence time of the FDDS in the stomach. This involved testing of formulations containing outer coatings containing a high percentage of hypromellose and outer coatings containing no nicotinamide as well as formulations containing an inner layer with a high percentage of starch.

Materials & Methods Nicotinamide was purchased from Sigma-Aldrich, hypromellose 400 mPa·s from Bufa, Starch 1500 from Colorcon and magnesium stearate from Genfarma bv. In all experiments demineralized water was used. The release profiles were determined in 0.01N HCl. For the preparation of coating suspensions acetone was used.

Hypromellose is a swelling agent that is used to delay the release of nicotinamide. The hydrophilic drug is released via diffusion. Starch and magnesium stearate show a faster release of nicotinamide. This influence of the various excipients has been investigated To prepare the floating delivery system, a suspension containing the excipients and the were drug sprayed on empty hollow capsules. This was done using a spray-coat system. The different substances are dissolved in water and acetone. The suspension should be slightly viscous to prevent sedimentation and blockage in the system. The ratio of acetone and distilled water depends on the amount of hypromellose. At a low concentration of hypromellose relatively more water is used so that the suspension has the desired viscosity. The substances are first suspended and/or dissolved in acetone prior to adding water. This prevents formation of lumps in the slurry. The suspension is sprayed through a nozzle (1 mm) together with air, so that small droplets are introduced into the spraying sphere. The spraying sphere is heated from the outside so that the acetone evaporates quickly and the substances are coated on the capsules. Capsule sizes 3, 4 and 5 (Spruyt Hillen) were used in various experiments. It was decided that capsule size 4 was used which were 'locked' by pressing the halfs together so as to somewhat reduce the size.

The coatings consisted of different formulations with different concentrations of nicotinamide, hypromellose, magnesium stearate and starch, as will be described here below.

The produced capsules were tested for their floating behaviour and release profile in a dissolution bath (Prolabo) filled with 1 liter 0.01N HCl, 37±1° C., at 50 rpm. The 0.01N HCl was prepared by degassing 6 liter of demineralized water and adding 8 ml 25% HCl. The release profiled were determined for at least 12 hours by UV absorbance measurements at 280 nm (cuvet 1 cm) (Ultrospec III, Pharmacia LKB). The floating behaviour was followed by visual inspection. All experiments were performed in 2-, 3- or 5-fold.

The final formulation for a 300 mg gradient FDDS comprises 3 layers. The first layer surrounding the capsule has a concentration of 80% nicotinamide (200 mg active). The second layer 50% (100 mg active), and the third layer 0% (90 mg coating material). The composition is shown in Table 2.

TABLE 2 composition of 300 mg nicotinamide FDDS.

| Component | 80% | 50% | 0% |
| --- | --- | --- | --- |
| Nicotinamide | 79% | 49% | — |
| Hypromellose | 16% | 40% | 78% |
| Starch 1500 | 4% | 10% | 20% |
| Magnesium stearate | 1% | 1% | 2% |
| Amount of active | 200 mg | 100 mg | — |

The final formulation for the 600 mg gradient FDDS comprises 2 layers. The inner layer consists of 80% nicotinamide. The layer comprises 750 mg of the coating material. Around it is a 0% coating of 150 mg. A SEM image was made of a cross-section of the FDDS in which both layers could clearly be distinguished. The composition of this FDDS is shown in Table 3.

TABLE 3 composition of 600 mg nictoinamide FDDS.

| Component | 80% | 0% |
| --- | --- | --- |
| Nicotinamide | 79% | — |
| Hypromellose | 16% | 78% |
| Starch 1500 | 4% | 20% |
| Magnesium stearate | 1% | 2% |
| Amount of active | 600 mg | — |

Results

Figure 1:
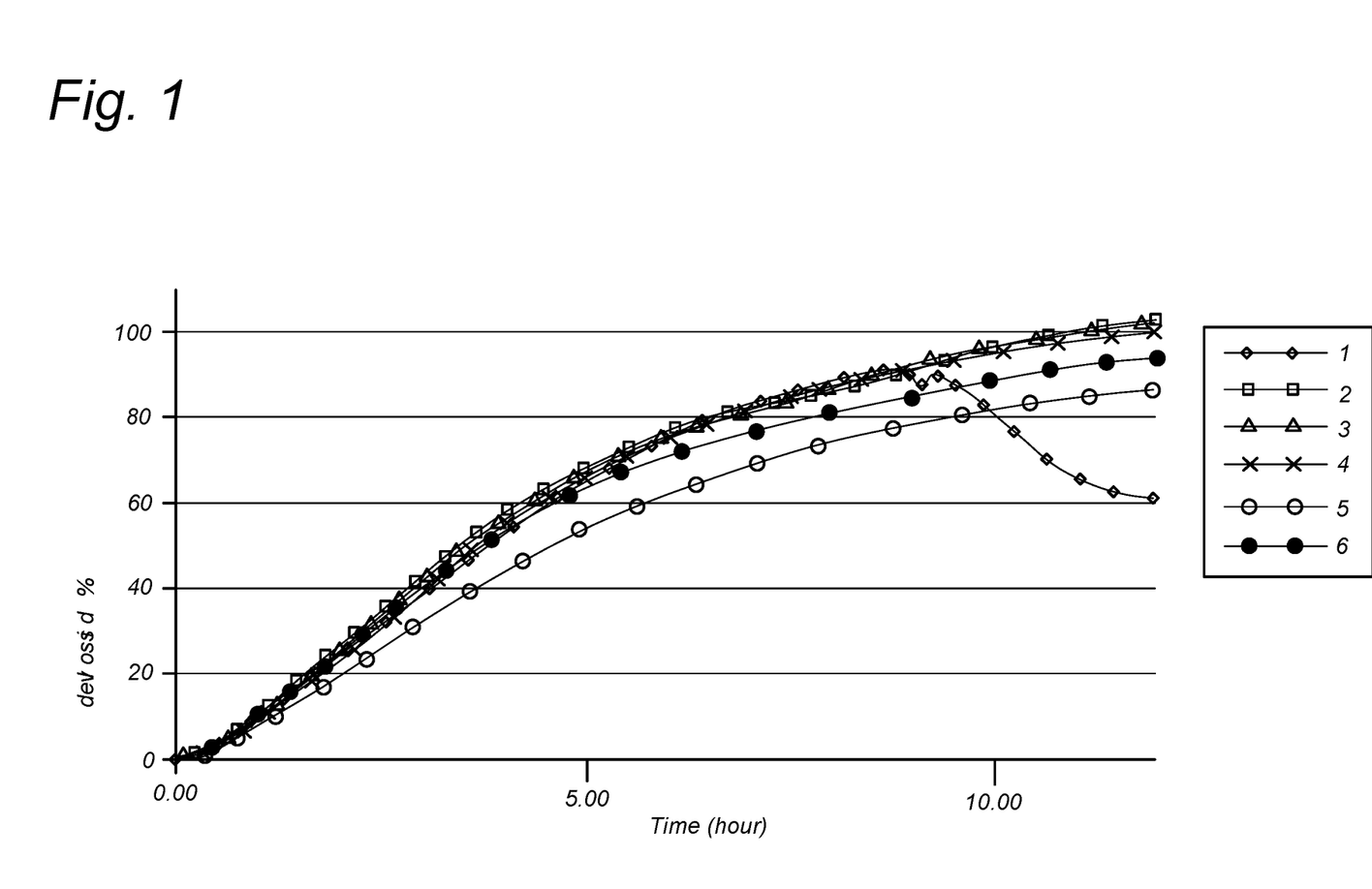
FIG. 1 shows the release profile of a 300 mg FDDS according to the invention.
Figure 2:
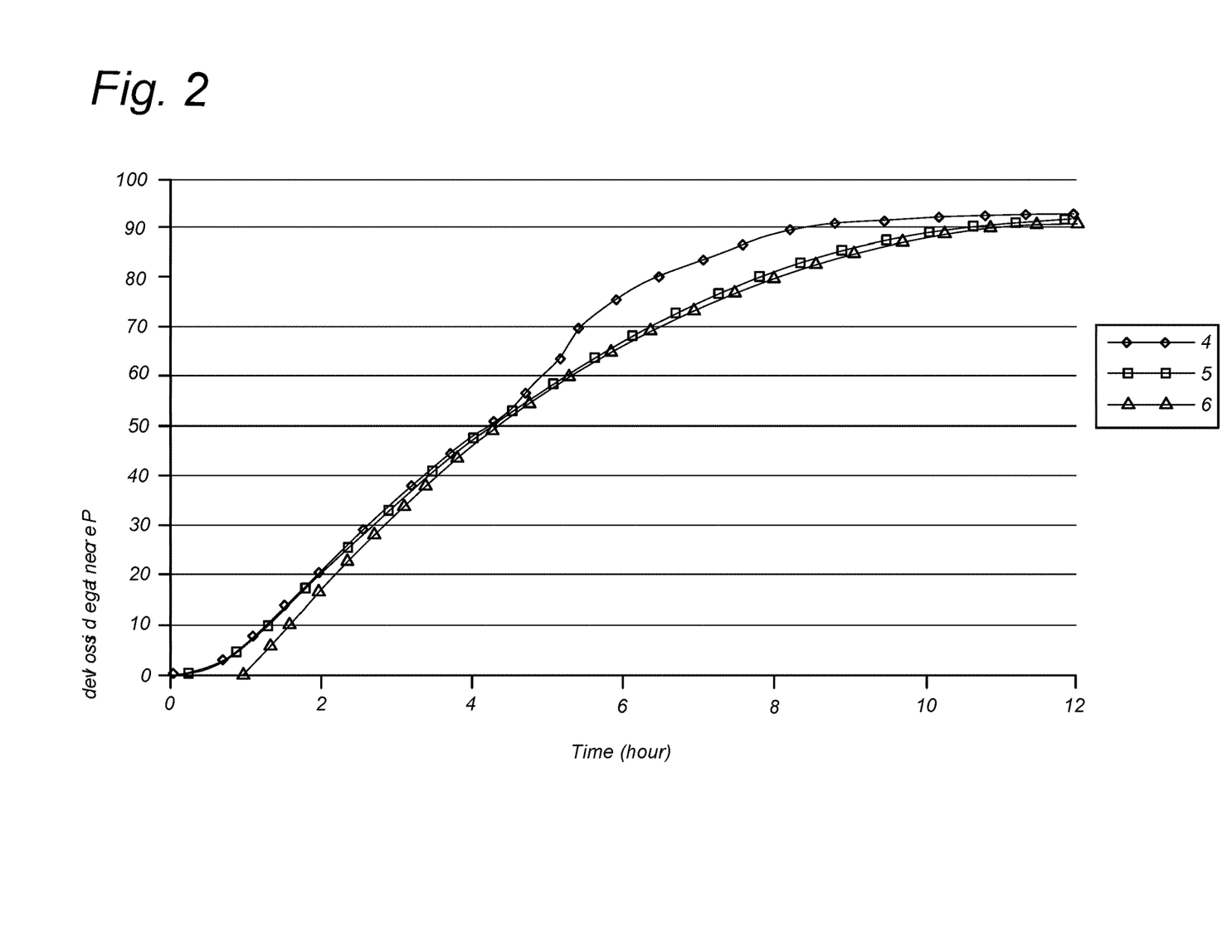
FIG. 2 shows the release profile of a 600 mg FDDS according to the invention.
Figure 3:
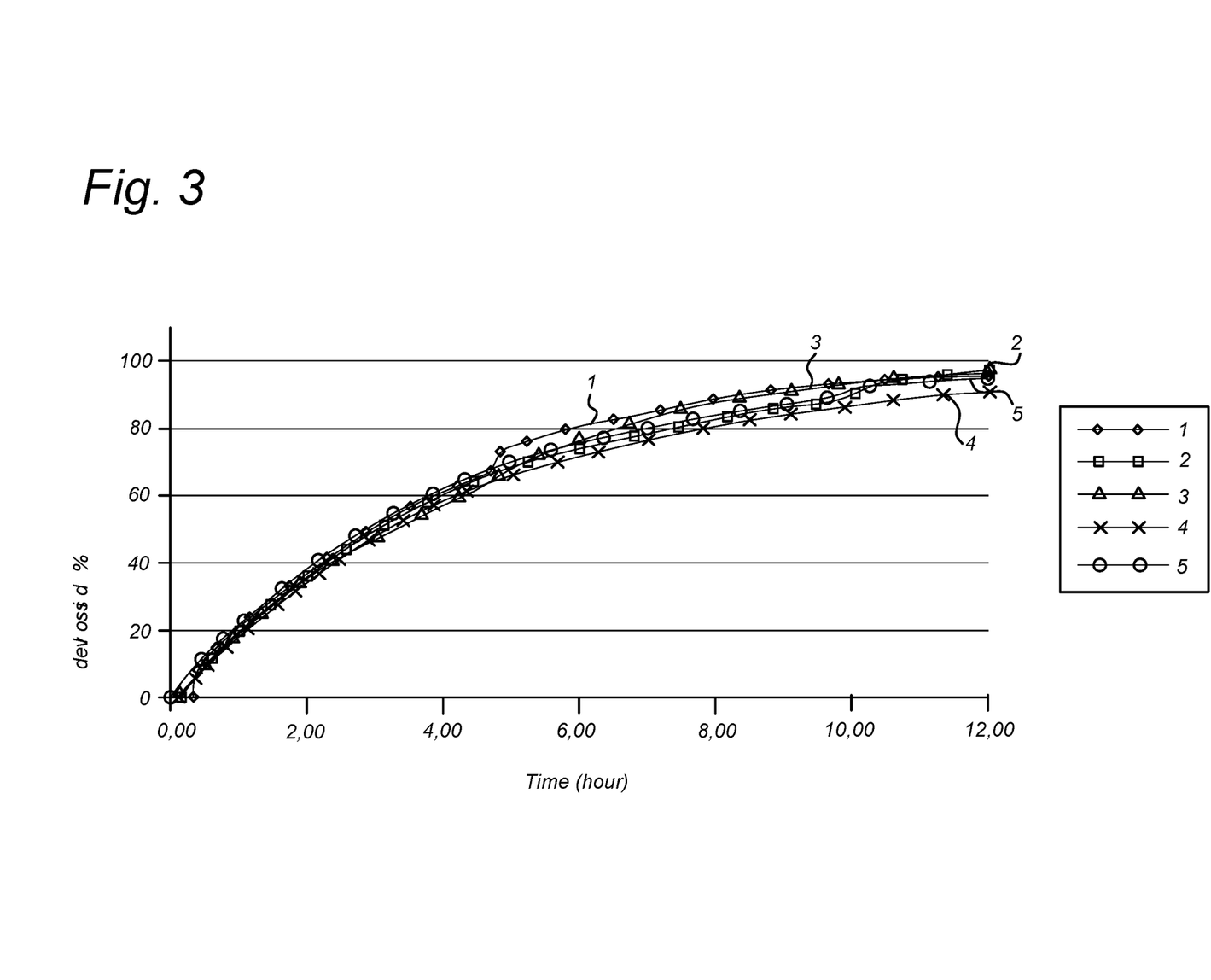
FIG. 3 shows the release profiles of ruptured and undamaged formulations according to the invention.

FIGS. 1 and 2 show the release profiles of the 300 mg FDDS and 600 mg FDDS respectively. A satisfactory release rate is accomplished nearly over the entire 12 hour period. The results show that the release profiles of the 300 mg 600 mg FDDS's are comparable.

The floating behaviour of both the FDDS's was also tested in milk, simulating an environment containing substantial amounts of fat. The FDDS's staid afloat for more than 12 hours.

Discussion/Conclusion

The 300 and 600 mg nicotinamide gradient FDDS's are capable of staying afloat for at least 12 hours and of releasing nicotinamide at a substantially constant rate for almost the entire 12 hour period.

To achieve this near constant release the FDDS's were designed to comprise different layers of coating. For example, the 300 mg FDDS contained an inner layer with 200 mg nicotinamide (80% based on the total weight of the layer), a middle layer with 100 mg nicotinamide (50% based on the total weight of the layer) and an outer layer that did not contain nicotinamide. The 600 mg FDDS contained an inner layer with 600 mg nicotinamide (80% based on the total weight of the layer) and an outer layer that did not contain nicotinamide.

The use of distinct layers allowed for the regulation of the overall release profile, to achieve near constant release rates of periods of up to 12 hours.

Example 4: Effects of Rupture of FDDS on Floating Capability and Release Profile Background The present inventors decided to also investigate the effects of mechanical damage to the FDDS. It was envisaged that damaging of the formulation could easily arise when treating young children as they might, for instance, 'accidentally' chew or crush the FDDS before swallowing. The floating behaviour and release profiles of ruptured capsules were therefore tested and compared to the floating behaviour and release profiles of intact FDDS's.

Materials & Methods

The FDDS's used for this experiment were of the multi-layer gradient type. They were prepared and tested using the protocols described in example 3. The composition is shown in Table 1.

TABLE 1 composition of FDDS for rupturing experiment

|  | 80% | 50% | 0% |
| --- | --- | --- | --- |
| Hypromellose | 16% | 19% | 78% |
| Starch 1500 | 4% | 10% | 20% |
| Magnesium stearate | 1% | 1% | 2% |
| Nicotinamide | 79% | 50% | — |

Each FDDS contained 45 mg 0% coating.

The FDDS's proved to be strong and difficult to damage. The FDDS's were placed in a bench vice that was tightened until the wall of the FDDS began to rupture.

The floating behaviour as well as the release profile was determined of both the damaged and undamaged the FDDS's.

Results

All FDDS's, ruptured and undamaged, staid afloat in the testing liquid. After 18 hours remains were still afloat in the dissolution beakers.

The release profiles of the FDDS's are shown in FIGS. 1 and 2. As can be seen in said figure, the release profiles of capsule 1 and 2 (undamaged FDDS's) did not differ significantly from that of capsules 3 and 4 (ruptured FDDS's). During the first 4 hours, the release profiles are identical. After 4 hours a minor difference becomes apparent in that the release rate of the ruptured FDDS is slightly higher than that of the non-damaged FDDS's. This difference is however is never more than 8%.

Conclusion/Discussion

The FDDS of the invention is capable of staying afloat even after mechanical damage and rupture. The damage hardly affects the nicotinamide release profile. Possibly, because of the swelling of the hypromellose upon contact with water, cracks in the wall are effectively closed restoring the integrity of the FDDS.

Example 5: In Vivo Release of Nicotinamide in Healthy Human Volunteers Using FDDS Healthy adults, 4 women and 4 men, were recruited as volunteers in a trial to investigate the pharmacokinetic profile of the nicotinamide FDDS of the invention. The trial was performed with 300 and 600 mg FDDS formulations as described in example 3.

During the trial blood was sampled at pre-determined intervals. Samples (Li-heparin) were collected and frozen for storage. In addition urine was collected (24 h). The entire protocol was as described in table 5.

TABLE 5

Protocol for determining PK profile of Nicotinamide FDDS

Figure 4:
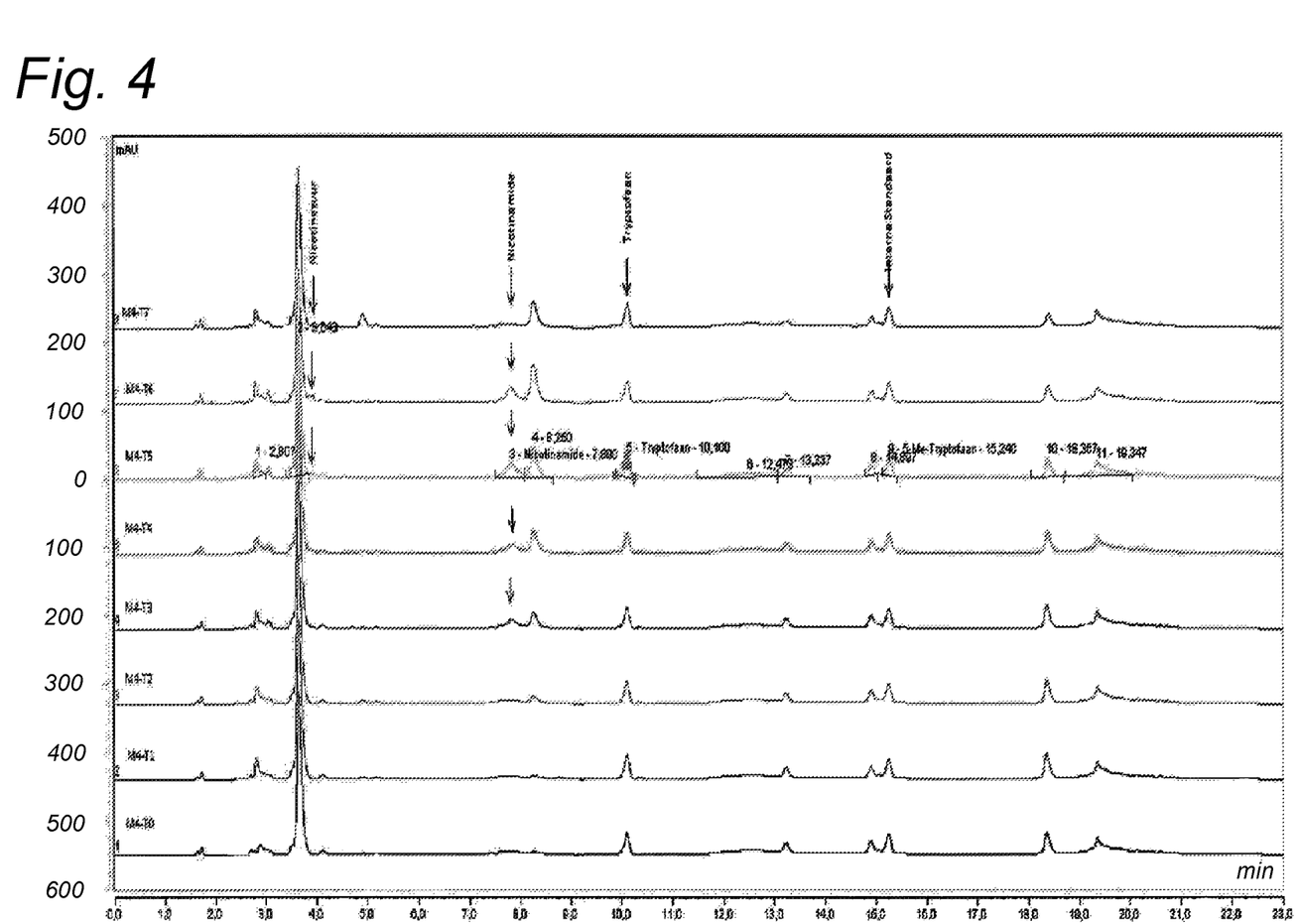
FIG. 4 shows the nicotinamide plasma level of a subject administered an FDDS according to the invention.

Start of trial
- 7:30 Arrival of subjects (empty stomach) at test location. Canule for blood sampling is placed.
  Blood sample T0
- 8:00 Subjects have breakfast (1-2 sandwiches) and drinks (tea, fruit juice)
- 8:15 Subjects ingest nicotinamide FDDS
- 8:45 Blood sample T1
- 9:45 Blood sample T2
- 10:45 Blood sample T3
  Subjects have drinks (tea, coffee, water and/or juice)
- 11:45 Blood sample T4
- 12:30 Subjects have lunch (3-4 sandwiches) and drinks ((tea, coffee, water and/or juice)
- 13:00 Blood sample T5
- 16:00 Blood sample T6
  Subjects have drinks (tea, coffee, water and/or juice)
- After Subjects go home. Subjects continue to collect their urine samples.
- 16:00 At home the subjects have dinner and drinks (standard) and are told not to take alcohol containing drinks
- 7:30 (next day) Arrival of subjects (empty stomach) at test location and hand over their urine samples.
- 8:00 Blood sample T7
End of trial The stored Li-heparin samples were analyzed using a standard HPLC measurement. Measurements were performed with and without protein removal from the plasma, as it appeared that the protein removal negatively affected resolution of the analyte(s). These problems, which could not be resolved instantaneously, did however not prohibit the detection of the nicotinamide in the various samples. For illustrative purposes, FIG. 4 is referred to, showing the detection of nicotinamide in the plasma of one of the test subjects. From this figure it can be inferred that the ingestion of the FDDS caused a significant and persistent increase in the subject's nicotinamide plasma level.

The overall results showed that the FDDS of the invention was capable of maintaining an increased nicotinamide plasma levels in vivo for a period of at least 8 hours after ingestion.

The invention claimed is:

1. A sustained release nicotinamide formulation in the form of a floating delivery system (FDDS), said FDDS comprising:
   i) an empty hollow capsule made of a polymer selected from the group of aqueous soluble, erodible, disintegrating and biodegradable polymers; and
   ii) two or more layers of coating surrounding the capsule, wherein at least one layer of the coating comprises 100-5000 mg nicotinamide;
   wherein the floating properties and sustained release profile of the FDDS in gastric fluid are maintained when the FDDS is mechanically damaged or ruptured.

2. The sustained release nicotinamide formulation of claim 1, wherein said two or more layers of coating are selected from the group consisting of coatings resistant to gastric juice, release-controlling coatings, and mixtures thereof.

3. The sustained release nicotinamide formulation of claim 2, wherein the release-controlling coatings comprise a swellable, poorly water-soluble or water-insoluble polymer;
   one or more enteric polymeric material(s);
   a mixture of at least two release controlling polymers; or
   a mixture of an enteric polymer, and a release controlling polymer.

4. The sustained release nicotinamide formulation of claim 2, wherein the release-controlling coatings comprise a mixture of hypromellose (HPMC) and starch as coating material.

5. The sustained release nicotinamide formulation of claim 1, having a density less than 0.95 g/cm$^3$.

6. The sustained release nicotinamide formulation of claim 1, wherein the capsule is a gelatin capsule or a HPMC capsule.

7. The sustained release nicotinamide formulation of claim 1, wherein the at least one layer of the coating comprises 250-5000 mg nicotinamide.

8. The sustained release nicotinamide formulation of claim 1, wherein the at least one layer of the coating comprises 500-5000 mg nicotinamide.

9. The sustained release nicotinamide formulation of claim 1, wherein said two or more layers of coating comprise a polymer that swells upon contact with water.

10. The sustained release nicotinamide formulation of claim 9, wherein said two or more layers of coating comprise hypromellose.

* * * * *